United States Patent
Dorronsoro Diaz et al.

(10) Patent No.: US 9,693,679 B2
(45) Date of Patent: Jul. 4, 2017

(54) MINIATURE SIMULTANEOUS VISION SIMULATOR INSTRUMENT

(71) Applicant: CONSEJO SUPERIOR DE INVESTIGACIONES CIENTIFICAS (CSIC), Madrid (ES)

(72) Inventors: Carlos Dorronsoro Diaz, Madrid (ES); Jose Ramon Alonso Sanz, Madrid (ES); Susana Marcos Celestino, Madrid (ES)

(73) Assignee: Consejo Superior De Investigaciones Cientificas (CSIC), Madrid (ES)

( * ) Notice: Subject to any disclaimer, the term of this patent is extended or adjusted under 35 U.S.C. 154(b) by 0 days.

(21) Appl. No.: 15/024,056

(22) PCT Filed: Sep. 25, 2014

(86) PCT No.: PCT/ES2014/070725
§ 371 (c)(1),
(2) Date: Jun. 23, 2016

(87) PCT Pub. No.: WO2015/049402
PCT Pub. Date: Apr. 9, 2015

(65) Prior Publication Data
US 2016/0296110 A1    Oct. 13, 2016

(30) Foreign Application Priority Data
Oct. 1, 2013    (ES) .................... 201331436

(51) Int. Cl.
*A61B 3/08* (2006.01)
*A61B 3/028* (2006.01)
(Continued)

(52) U.S. Cl.
CPC .......... *A61B 3/0285* (2013.01); *A61B 3/0025* (2013.01); *A61B 3/028* (2013.01);
(Continued)

(58) Field of Classification Search
USPC .......................... 359/627–636; 351/200–246
See application file for complete search history.

(56) References Cited

U.S. PATENT DOCUMENTS 7,131,727 B2    11/2006    Jones et al.
2006/0081793 A1*    4/2006    Nestorovic ........ G02B 27/0172
250/580

(Continued)

FOREIGN PATENT DOCUMENTS

EP    0199218 A2    10/1986
JP    2009178500 A    8/2009
(Continued)

*Primary Examiner* — Mohammed Hasan
(74) *Attorney, Agent, or Firm* — McNees Wallace & Nurick LLC (57) ABSTRACT

The invention relates to a miniature simultaneous vision simulator instrument with various image-forming channels, each one of which projects, onto the retina of the same eye, a component image with a different degree of defocusing of the same observed object, such that the superposition of all of the component images forms a final simultaneous vision image on the retina of the eye. The instrument has at least one adjustable variable focus lens that, as the focus is changed, modifies the vergence of the light beam passing through said adjustable lens. Furthermore, one of the image-forming channels passes through the adjustable variable focus lens. The instrument can operate in the modality of optical channels that are physically differentiated in the modality of temporal channel multiplexing.

14 Claims, 4 Drawing Sheets

(51) Int. Cl.
  *A61B 3/00*  (2006.01)
  *G02B 27/02* (2006.01)
  *G02B 27/10* (2006.01)
  *A61H 5/00*  (2006.01)
(52) U.S. Cl.
  CPC ............... *A61B 3/08* (2013.01); *A61H 5/005* (2013.01); *G02B 27/022* (2013.01); *G02B 27/106* (2013.01)

(56) References Cited

U.S. PATENT DOCUMENTS

2006/0285074 A1    12/2006  Jones et al.
2014/0155999 A1*    6/2014  Vidal Canovas ... A61F 9/00802
                                                  623/6.27

FOREIGN PATENT DOCUMENTS

| WO | 2004/049927 A1 | 6/2004 |
| WO | 2010/116019 A1 | 10/2010 |
| WO | 2012/055049 A1 | 5/2012 |

* cited by examiner

MINIATURE SIMULTANEOUS VISION SIMULATOR INSTRUMENT

FIELD OF THE ART

The present invention relates, generally, to the field of visual optics, and in particular to the field of ophthalmic corrections to compensate for presbyopia.

STATE OF THE ART

The young human eye has the ability to change its focus to see sharply both near and far objects. This ability of the eye, called accommodation, is achieved because the crystalline lens is capable of changing its focus, changing the shape of its surfaces. The loss of accommodation that occurs with age is called presbyopia. The signs of presbyopia start to appear before the age of 45 and cause the entire population over the age of 55 to depend on optical corrections of some sort to see properly from far and near distances. The most common presbyopic correction is ophthalmic lenses, either in the form of reading glasses, spectacles with bifocal segments or progressive lenses. Despite being the most immediate solution to the problem of presbyopia, spectacles are far from being considered an optimal solution, for aesthetic or discomfort reasons.

Over the past decades, alternative optical corrections have been developed to alleviate the effects of presbyopia, which in one way or another seek to provide a sharp image of near objects eliminating partially or totally the dependence on spectacles. Some of these solutions are based on the concept of simultaneous vision. Corrections based on simultaneous vision overlap two or more component images on the retina to form the final image. One of the component images corresponds to a viewing distance of far vision and other component image corresponding to a viewing distance of near vision. The increase of optical power required for focusing at the distance of near vision (determined by the particular ophthalmic correction) with respect to the power required for far vision is called 'addition'. The resulting final image of observing an object at a certain distance through a simultaneous vision correction is formed, in the best case, by a sharp component in focus, superimposed over one or more unfocused components, out of focus, leading to a general loss of contrast in the image. Simultaneous vision solutions, bifocal, multifocal or progressive, are incorporated into different types of corrections such as contact lenses, intraocular lenses or corneal refractive laser surgery patterns. These solutions have aesthetic advantages over spectacles, since they can barely be seen from the outside and, besides, are very comfortable for the user.

Besides the use in adults to compensate for presbyopia, simultaneous vision contact lenses are also used in child population in order to prevent the appearance of myopia or slow down its progression. This use of bifocal contact lenses is based on a theory suggesting that myopia appears and develops as a result of a forced use of the accommodation system in response to an excess of near vision. Simultaneous vision lenses relax the use of the patient's accommodation system and, on this basis, by prescribing simultaneous vision lenses to child population it is intended to prevent the appearance of myopia or slow down its progression.

However, not everyone is able to tolerate the degraded final image provided by these solutions. For contact lens fitting a trial-and-error process is followed. Different designs are adjusted on the patient, who tests them for a while, until he can tolerate some of them. The procedure is expensive and inefficient, since patients who are intolerant to simultaneous vision solutions are only identified at the end of the process, when all proposed designs have finally been rejected. The situation is much worse in the case of surgical solutions, such as intraocular lenses implantation or corneal laser ablation with a multifocal pattern, since these procedures are either irreversible or require any intervention to be performed in the surgery room.

Hence, it arises the need to simulate simultaneous vision, non-invasively and as accurately as possible, providing the patient with two or more images with different degrees of focus, but similar size, that overlap to produce a simultaneous vision image of the observed object. Thus, the patient is provided with a visual experience of pure simultaneous vision, isolated from problems associated with the particular ophthalmic correction such as decentering tilts, or other specific problems such as bending or contact lenses conformity, applying laser energy in corneal refractive surgery or scarring effects in surgery techniques. This is an ideal approach to anticipate, prior to the actual use of simultaneous vision corrections, the visual problems that each patient will experience, either optical or neuronal, and to predict which patients will not tolerate simultaneous vision solutions.

To simulate simultaneous vision two or more channels must be necessarily used, in each one of which a different defocus is introduced, to generate two or more component images of the same scene, each image having a different degree of blur. The final simultaneous vision image is formed by overlapping these component images, ideally all in the same position on the retina, and of the same size. The simulation can be performed digitally, with component images in which the different degrees of focus are simulated by image processing, or by optical methods, by using optical instruments that induce actual defocus. In the latter case, the optical coupling between the simultaneous vision correction and the optics of the particular patient's eye is simulated mole realistically. Accurate simulation requires optical channels perfectly aligned and generating the same magnifications.

Up to the present day, the approaches followed for simulating simultaneous vision corrections with optical methods (Jones and Such in U.S. Pat. Nos. 7,131,727 and 7,455,403; Dorronsoro and Marcos in WO/2010/116019) are based on the use of physically differentiated optical channels, and both the division and recombination of the channels are based on optical beam splitter components. Up to now, the changes of vergence in the different optical channels have been induced by the displacement of passive optical elements such as lenses and mirrors. In the case of WO/2010/116019 patent, the projection is performed by at least one Badal system that provides a correct coupling between the pupils of the instrument and the subject's pupil. For every Badal system two beam splitters, two mirrors and two projection lenses are typically needed. The displacement of several moving elements of the Badal system allows changing the effective distance between the projection lenses and provides changes in vergence without modifying the magnifications, and finally an identical retinal size of the component images.

The displacement of optical elements requires the use of mechanical displacing platforms with a very high degree of optical precision, to avoid mismatching between channels and errors in the superposition of the final simultaneous vision image. Furthermore, it is convenient that such platforms are motorized, in order to induce vergence and defocus quickly and accurately. All of this raises the cost of the final simultaneous vision instrument, and at the same time it involves large volume and weight.

Besides, as the division and recombination of the channels are based on beam splitters, the number of possible channels is very limited, due to physical space limitations, light losses and alignment problems, Normally only bifocal solutions are simulated by physically differentiated channels, as only two channels are required. By increasing the number of channels multifocal solutions might be explored, although this greatly increases cost, weight and volume of the instrument. But the simulation of progressive optical corrections is beyond the scope of this approach based on physically differentiated optical channels, since it would require the use of innumerable channels, with a continuous variation of defocuses.

There is need for a workable system with low weight and size, and portable, through which the patient can intuitively experience simultaneous vision. A miniaturized system would also allow the possibility of freely moving while experiencing simultaneous vision. In addition, a system of small size and low weight would facilitate the realization of optometric tests in an optometry or ophthalmology clinic. Likewise, the evolution of the simultaneous vision corrections market increasingly reinforces the necessity of simulating not only bifocals solutions but also multifocal and progressive ones.

Current simultaneous vision simulators do not meet the needs of low weight and volume at low cost, nor can emulate multifocal solutions, as already mentioned, it is not likely either that new systems based solely on conventional optical elements might meet these needs. t is necessary to incorporate new technologies that facilitate the miniaturization of simultaneous vision simulation instruments, and in particular to eliminate the need for using motorized displacing platforms.

In recent years adjustable lenses, also called variable focus lenses, have been developed, which are able to change their focus in a controlled manner. Recently, new realizations of these adjustable lenses have been launched (Kern in WO/2012/055 049) in which the change of focus comes in response to an electrical pulse, and therefore they can he automated easily and controlled remotely. In addition, these lenses can work at very high speed and meet the requirement of reduced cost demanded for this application.

DESCRIPTION OF THE INVENTION

Brief Description

A simultaneous vision simulator comprises at least two image-forming channels, each one of which projects on the retina of the same eye a component image of the same observed object with different degrees of defocus, so that the superposition of all the component images on the retina forms a final simultaneous vision image. The present invention is based on the use of an adjustable variable focus lens as pad of a simultaneous vision simulator to change the degree of defocus of at least one of the component images. Of the two or more image-forming channels, in the miniaturized instrument object of this invention at least one of them passes through an adjustable variable focus lens, which by changing its focus modifies the vergence of the light beam passing through said adjustable lens.

Figure 1:
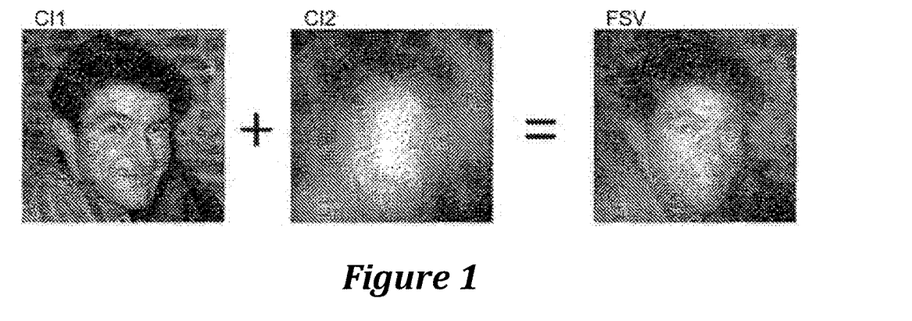

FIG. 1 shows with an example the visualization of the result expected to be obtained with simultaneous vision simulators. A first component image [CI1], resulting from projecting through a first image-forming channel and with a certain vergence the image of an object in the retina of the eye so that the retinal image is focused, is added to a second component image [CI2], resulting from projecting through a second image-forming channel and with a different vergence the image of the same object on the retina of the same eye so that the retinal image is blurred, in such a way that the superposition of the two component images [CI1 and CI2] form the final simultaneous vision image [FSVI]. The final simultaneous vision image [FSVI] produced by the simultaneous vision simulator, as observed in FIG. 1, is a degraded image equivalent to the real image provided by simultaneous vision corrections. It is characteristic of this invention that the degree of focus of at least one of the component images, and therefore the beam vergence forming said component image, is given by an adjustable variable focus lens. The use of an adjustable variable focus lens makes the miniaturized simultaneous vision simulator instrument object of this invention differ from previous approaches of simultaneous vision simulation in which the induction of vergence changes in the channels was based on the change of the relative distance between optical elements, and therefore the dependency on the use of moving platforms and motors introducing significant increase in cost, weight and volume is removed. This approach based on the use of at least one adjustable lens therefore facilitates miniaturization of simultaneous vision simulation instruments and allows the development of low volume and weight systems, at a cost comparable to the previously existing ones.

One of the various forms of realizing the invention is the implementation of physically differentiated optical channels, wherein the image-forming channels are provided to the eye by at least two physically differentiated optical channels. In this invention, in at least one of the image-forming channels an adjustable lens is located that changes the vergence of the beam passing through it and therefore the vergence of the corresponding image-forming channel. As an example, the physical differentiation of the physically differentiated optical channels can be generated by optical beam splitters that divide each beam into two different beams, a reflected beam and a transmitted beam.

Additionally, in this invention a new concept is proposed for generating simultaneous vision images, called temporal channel multiplexing, which allows for the first time simultaneous vision simulation with progressive power profiles. Temporal channel multiplexing consists of inducing with the adjustable lens a periodic temporal variation of the vergence of the light beam passing through it. Different levels of vergence, repeated periodically, define different temporal channels, each temporal channel being an image-forming channel that projects a component image of the observed object on the retina with a different degree of defocus corresponding to the beam vergence. Temporal channels are temporally multiplexed at a frequency higher than the fusion frequency of the eye and the spacio-temporal superposition of all the component images forms a final simultaneous vision image that is perceived as static. Temporal channel multiplexing can complement or even replace the channel decomposition by means of the modality of optical beams division used in previous patents for simulating simultaneous vision.

Temporal channel multiplexing for simulating simultaneous vision can be implemented with different technological solutions, and the use of adjustable lenses able to induce rapid changes in focus constitutes an ideal solution since simultaneous vision can be induced with adjustable lenses without introducing energy losses or alignment problems. In addition, since in the modality of temporal channel multiplexing by means of adjustable lenses it does not exist the space limitations of the physically differentiated optical channels, as many temporal channels as desired can be introduced, always within the operating speed limits of the lens, allowing simulating simultaneous vision with different power profiles, particularly bifocal, multifocal or progressive power profiles.

One possible use of the system in an optometry or ophthalmology clinic is the evaluation of candidates for multifocal simultaneous vision correction. When a patient in a clinic is considered to be a candidate for simultaneous vision correction, a visual test of tolerance or acceptance to such correction can be performed with the simultaneous vision simulator instrument object of this invention. Visual tests can also be performed to determine some parameter of the correction. These tests may be performed prior to surgery or contact lenses adaptation, and are conducted in a strictly non-invasive manner, without touching the eye.

During the test the patient is asked to look through the instrument at a particular object, which can be an eye chart, or any other object. After a short adaptation period, during which the subject gets used to the new visual experience, the examiner conducts a subjective visual examination based on a series of questions and tests, similar to those of other subjective visual examinations. The visual test may be based on questionnaires or may consist of psychophysical experiments with varying degrees of sophistication, in order to assess the impact of the image degradation on the subject's vision, to estimate the tolerance of the subject to the type of image he experiences, or to determine some parameter of the optimal correction for the subject.

An additional object of the present invention is to provide an embodiment example of the invention that contains the optical and mechanical design of a miniaturized simultaneous vision simulator instrument based on both temporal channel multiplexing by means of an adjustable lens and physically differentiated optical channels. The design of the mechanical elements holding and aligning the optical elements of the instrument is included. The solutions adopted in the mechanical design of the instrument, and the arrangement of the elements of the embodiment example of the invention, are essential to achieve the miniaturization pursued in this invention.

DETAILED DESCRIPTION OF THE INVENTION

One of the objects of this invention is a miniaturized simultaneous vision simulator instrument comprising at least two image-forming channels, each one of which projects onto the retina of the same eye one component image with different degree of defocus of the same object, so that the superposition of all component images forms on the retina of the eye a final simultaneous vision image, characterized by comprising at least one adjustable variable focus lens that modifies the focal vergence of the light beam passing through the adjustable lens, and where at least one of the image-forming channels crosses the adjustable variable focus lens.

In one embodiment of the invention, at least two of the image-forming channels are provided to the eye through two physically differentiated optical channels, and at least one of them has an adjustable lens in it.

Figure 2:
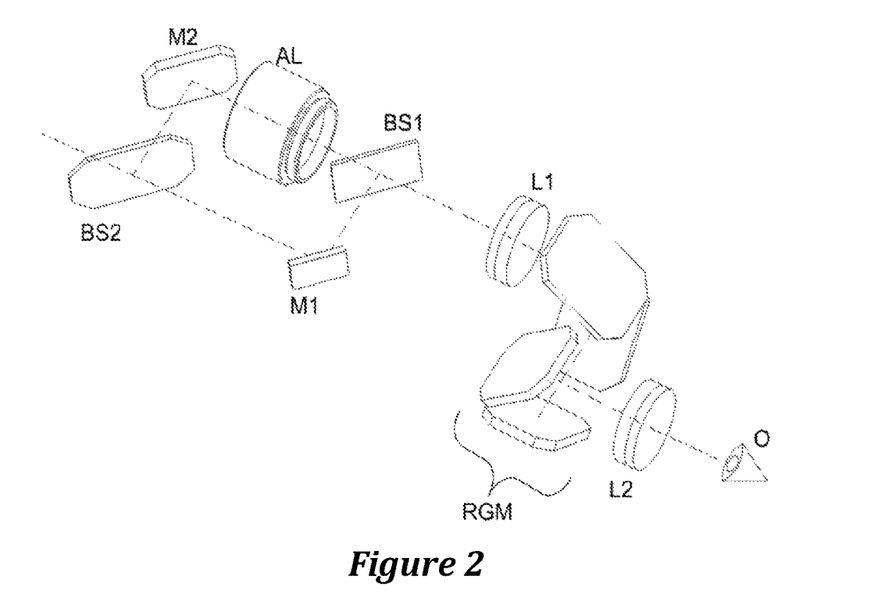

FIG. 2 schematically shows, without limitation, an explanatory example based on this physically differentiated optical channels solution, with two physically differentiated optical channels that are generated by means of a beam splitter [BS1]. In one of the optical channels an adjustable lens [AL] is located, and this optical channel is considered the near vision image-forming channel. The other channel, which contains no adjustable lens, is considered the far vision image-forming channel. A second beam splitter [BS2] recombines the optical channels, which remain coincident in the section between the object and the simultaneous vision simulator instrument. Since the different vergences are introduced in the near vision image-forming channel by the adjustable lens, it is not necessary to move the optical elements for inducing addition (defocus in the component images) although it is convenient to maintain mobility of the elements in order to compensate for possible refractive errors of the patients using the instrument. Furthermore, the use of such projection solutions leaves sufficient space between the system and the eye of the patient so that, if necessary, the patient can wear their own spectacles while performing the experiment. Astigmatism can be corrected by means of trial lenses. These projection systems also facilitate that simultaneous vision simulators based on the invention may be used in combination with a phoropter.

The energy balance between both channels, to provide different weight to the near or far vision channels in the simulation, can be modified by the relationship between transmittance and reflectance in the beam splitter, or through neutral filters inserted into one channel.

There is the possibility to provide, immediately and at any time, the simulation of a monofocal correction, simply by blocking completely one of the physically differentiated optical channels. The monofocal vision can be considered a reference condition during the clinical trials of the instrument, with which the performance of simultaneous vision can be compared and therefore instant accessibility is important.

The far vision channel of the embodiment shown in FIG. 2 leaves free a pupil plane where a second adjustable lens or trial lens can be placed, providing more flexibility for correcting the refractive errors of the patient, including astigmatism. Trial lenses can also he placed along with the adjustable lens to shift the power range that the latter may generate. Apart from trial lenses, or in their place, artificial pupils can be introduced in the pupil planes of the different channels to segment the pupil region in which the correction of each channel is applied. Pupil diameter in which both far vision and near vision are applied can be simply limited, but other uses can also be considered such as testing the image quality of the simultaneous vision through the pupil periphery or applying a channel through the central area of the pupil and another channel at the peripheral zone. This can be performed using transmission masks with different segmentations or by means of polarizing elements that deflect the light through either pupil channel following a certain pupil pattern. The polarizing elements can be either passive optical elements, for example polarizing plates, filters or cubes, or active polarizing elements such as computer-driven liquid crystals that control the polarization at each point of a plane. Either by artificial pupils or other transmission masks, or by means of active or passive polarizing elements different segmentation patterns can be incorporated in the miniaturized device, like those already existing in the market: central addition, peripheral addition, bifocal segments, hemifields, alternating power rings.

Figure 3:
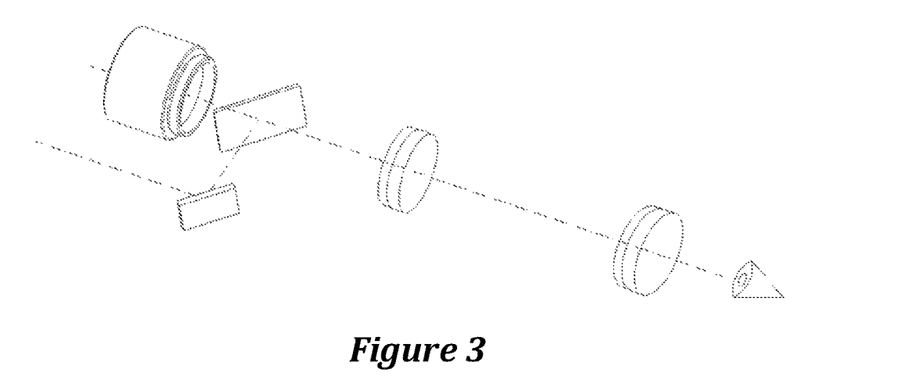
FIG. 3.—Device of the invention in which the optical channels are kept separate in the section from the object to the instrument, and without a reversing group of elements. The first lens [L1] and the second lens [L2] project the adjustable lens [AL] on the pupil of the eye [E]. The beam splitter [BS1] generates two physically differentiated optical channels, and the mirror [M1] makes both channels to be collinear and point to the same object. Physically differentiated optical channels are kept separate in the section from the object to instrument.

The embodiment of the invention shown in FIG. 2 is only an example of the multiple embodiment possibilities of the invention by means of physically differentiated optical channels. For example, FIG. 3 shows a simplified embodiment with respect to FIG. 2 one, in which the optical channels are kept separate in the section between the instrument and the object.

Figure 4:
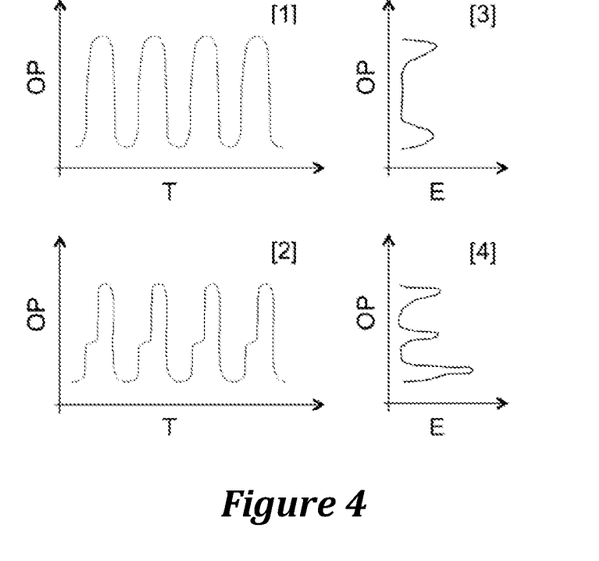

Another object of this invention is a simultaneous vision instrument based on temporal channel multiplexing. In this modality of temporal channel multiplexing different simultaneous vision ophthalmic corrections can be simulated, depending on the temporal histogram of the used focuses. In FIG. 4 both the periodic profiles of optical power level covered by the lens ([1] and [2]), and the corresponding histograms of the energy integrated over time for each optical power ([3] and [4]) are illustrated, showing the energy perceived by the observer corresponding to each optical power. Using only two power levels between which the adjustable lens alternates in time at high speed [1], bifocal lens corrections with two peaks in the energy histogram for each optical power can be simulated [3]. Sweeping along a discrete set of optical powers multifocal solutions can be simulated, for example by sweeping over time three power levels [2], trifocal solutions are simulated [4]. And going over a certain time profile with a continuous power variation between a maximum and a minimum, any progressive through focus power profile is simulated without additional difficulty and the limitation of using a small number of channels, existing prior to this invention, is overcome for the first time.

It is worth noting that this temporal channel multiplexing modality is only possible when the optical power can vary at high speed, as happens with the use of a high-speed adjustable lens. The adjustable lens provides different powers over time, but it does it so quickly that the eye is not able to discriminate those temporal differences and fuses (recombines) all the component images into one final simultaneous vision image.

The physical channel that supports this temporal channel multiplexing with adjustable lens is always the same, the physical channel where the adjustable lens is located, and the temporal channels are given by the optical powers the adjustable lenses adopt in its periodic sweep of powers.

Temporal multiplexing allows to easily changing the energy balance between channels, simply by changing the balance between the times allocated to each temporal channel. In the example of temporal multiplexing of FIG. 4, the bifocal lens has an equitable energy distribution between optical powers [3] because the lens spends a similar amount of time on both optical power levels [1]. However, in the trifocal lens example, unequal distribution of times between the three levels of optical power [2] results in an energy imbalance between the different optical powers.

The simulation of a monofocal lens in the temporal multiplexing modality is achieved with no energy loss, simply by stopping the adjustable lens.

In the temporal multiplexing option, the spherical error of the patient, i.e. its myopia or hyperopia, can be corrected by moving the optical power profile of the adjustable lens until it provides the patient with a suitable optical power profile, corresponding to the patient's near and far vision distances.

Although the embodiments shown in FIGS. 2 and 3 are based on the modality of physically differentiated optical channels, they can additionally operate in the modality of temporal channel multiplexing, based on the high-speed optical power sweep of the adjustable lens. This way, the near vision channel becomes a multifocal or progressive channel, keeping sharp the image component in the far vision channel.

Figure 5:
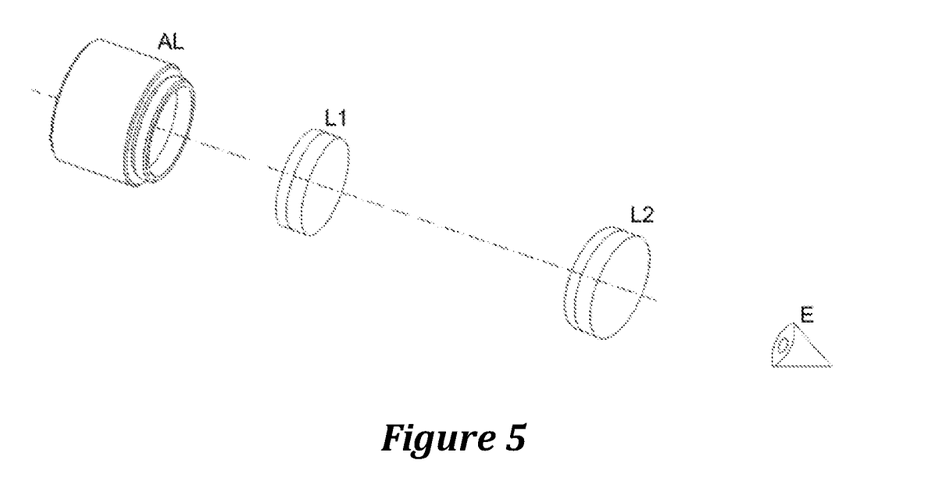
FIG. 5.—Device of the invention exclusively based on the modality of temporal channel multiplexing, on the physical basis of a single optical channel and on an adjustable lens. The adjustable lens [AL] is directly projected on the pupil of the subject's eye [E] by the projection lenses [L1 and L2].

Embodiments of the invention solely based on the modality of temporal cannel multiplexing are also possible, on the physical basis of a single optical channel. FIG. 5 shows such an embodiment. No beam splitters are used and the adjustable lens, which is directly projected on the pupil of the eye, represents the only mechanism for generating the component images. Therefore, the adjustable lens must beat optical powers corresponding to both far and near vision to induce in the patients the simultaneous vision experience. It is therefore necessary that the fundamental element, the adjustable lens [AL], meets strict specifications for operating speed and power range. In addition, while being used in this temporal multiplexing mode, the adjustable lens [AL] is subject to rapid changes that occur at very high speed and can generate inertia and wear that could compromise image quality.

Temporal multiplexing is also theoretically accessible without adjustable lenses. An alternative approach to the use of adjustable lenses is temporal multiplexing using one or more oscillating mirrors, which can oscillate in axial position (such as piezoelectric mirrors) or tilt (such as galvanometric mirrors). With these alternative approaches vergence changes are achieved, rather than by changing the focus, through the variation of the optical path within a channel or through physically differentiated channels alternation, at high speed.

Although the instrument is designed for assessing the visual quality observing objects at far distances, it can also be used for observing objects at intermediate and near distances by simply readjusting power projection, but it has to be taken into account that the effective viewing distance is the distance from the adjustable lens to the instrument, and not the distance from the eye to the object. For example, the evaluation of the image quality of a text at "reading distance" should be performed by placing the text at a reading distance of the plane in which the adjustable lens is placed, which in practice can be approximated by the plane of the closing window of the instrument, if it exists.

A miniature binocular simultaneous vision simulator can be built from two monocular system components entirely fixed by means of an assembling mechanical part. Preferably, this assembling mechanical part allows adjusting the separation between the monocular system components to match the interpupillary distance of the patient.

The instrument can have different uses. First, it can he used to detect presbyopic patients who are not good candidates for simultaneous vision ophthalmic corrections because of their intolerance to image degradation. The instrument can also be used as a tool to provide training to the patient and support the optometrist or ophthalmologist on their explanations of simultaneous vision, thereby promoting informed decision-making by the patient on the parameters of the ophthalmic correction to use, for example addition. The patient can also use the system for previous non-invasive training of the simultaneous vision experience. The system can be used in research, design and testing of new multifocal ophthalmic corrections.

The instrument can be used in combination with other visual tests (such as visual acuity or contrast sensitivity) or more sophisticated psychophysical procedures, or in combination with surveys or questionnaires.

The instrument can also be used in combination with other instruments such as a phoropter. The instrument can also be used as a phoropter itself. Thanks to the ability of the adjustable lens, through which the observer sees, to change its focus, the instrument can be used to provide successively different power corrections to the observer and evaluate his subjective preference.

The instrument can be used in combination with a computer that generates visual psychophysical tests with which the simultaneous vision performance of the patient can be evaluated, as well as his degree of satisfaction. The simultaneous vision simulator system and the computer can be connected by cable or wirelessly, or not connected at all.

DESCRIPTION OF THE FIGURES

FIG. 1.—Visualization of the result expected to be obtained with simultaneous vision simulators, by means of an example. A first component image [CI1] resulting from projecting the image of an object on the retina with a certain vergence via a first image-forming channel so that the retinal image is focused, is added to a second image component [CI2] resulting from projecting the image of the object on the retina with a different vergence via a second image-forming channel so that the retinal image is out of focus, in such a way that the superposition of both component images [CI1 and CI2] forms the final simultaneous vision image [FSVI].

FIG. 2.—Device of the invention with two physically differentiated optical channels. The beam from the object is split into two physically differentiated optical channels by a beam splitter [BS2]. One channel contains the adjustable lens [AL] and is considered the near vision channel. The other channel, which contains no adjustable lens, is considered the far vision channel. Two mirrors, one in each channel [M1 and M2], direct the beams to a beam splitter [BS1] where they are recombined into a single optical beam passing through a pair of projection lenses [L1 and L2], which project the adjustable lens [AL] on the patient's eye [E] pupil. To compensate for the fact that the projection system reverses the image in two axis, between the first lens [L1] and the second lens [L2] a reversing group of mirrors [RGM] is placed, which reverses the image both vertically and horizontally, making the system more compact at the same time.

FIG. 4.—Illustration of the operation of the invention in the modality of temporal channel multiplexing. This figure shows both the periodic profiles of optical power levels covered by the lens ([1] and [2]) and the corresponding histograms of the energy integrated over time for each optical power [3 and 4], which illustrates the energy perceived by the observer corresponding to each optical power. Using only two power levels between which the adjustable lens alternates in time at high speed [1], bifocal solutions with two peaks in the energy histogram for each optical power can be simulated [3]. Sweeping along a discrete set of powers multifocal solutions can be simulated, for example by sweeping over time three power levels [2] trifocal solutions are simulated [4]. And going over a certain temporal profile with a continuous power variation between a maximum and a minimum, any progressive through focus power profile is simulated without additional difficulty and the limitation of using a small number of channels, existing prior to this invention, is overcome for the first time.

FIG. 7.—Device of the invention with two physically differentiated optical channels, according to FIG. 2, showing with more detail the main elements of the design. The projection system, with the first lens [L1], the reversing group of mirrors [RGM] and the second lens [L2] (not shown in the drawing, but located after the reversing group of Mirrors [RGM]) is grouped in an ocular block [OB], which also contains an eyecup [EC]. The position of the trial lenses [TL] in the far vision channel is also displayed, which constitute an additional mechanism to compensate for refractive errors, including astigmatism, and for which the system has a specific support. The optomechanical components holding and positioning the optical elements [BS2 and M2] that are more important for the alignment between channels are also shown. The system contains a closing glass window [CW].

FIG. 8. Device of the invention with two physically differentiated optical channels according to FIGS. 2 and 7, with more detail. Two complementary views of a single monocular system are shown, with a bottom housing where all elements constituting the system are supported. The support or coupling pieces between the optical elements and the housing are shown. The support system for the trial lenses occupies the central part of the instrument and consists of a rotating wheel [W] with which the angle of the astigmatism-correcting lens can be regulated. The ocular block has also a mark [MK] and scale, indicating the diopters of spherical refractive error compensated for the patient.

EMBODIMENT EXAMPLE OF THE INVENTION

As a case study of embodiment of the invention, and without limitations, various embodiments of miniature simultaneous vision simulator instrument are described below, implementing in a simple way the main concepts object of this invention.

In all the examples an adjustable lens is used, which is capable of changing the curvature of one of its polymeric material faces at high speed in response to an applied electrical current. It has an optical aperture of 10 mm and is capable of going over an optical power range of more than 10 diopters. The adjustable lens has a high transmission coefficient in the visible spectrum and provides high image quality in relation to the optics of the eye, as it has reduced aberrations, both chromatic and geometric. The adjustable lens exhibits high repeatability in terms of power versus applied current.

Example 1

FIG. 2 shows an embodiment of the invention based on the use of an adjustable lens [AL] in a simultaneous vision simulator operating in the modality of physically differentiated optical channels, which may further operate as temporal multiplexing modality. The beam from the object is split into two physically differentiated optical channels by a beam splitter [BS2]. One channel contains the adjustable lens [AL] and is considered the near vision channel. The other channel, which contains no adjustable lens, is considered the far vision channel. A mirror in each channel [M2 and M1] direct the beams to a beam splitter [BS1] where they are recombined into a single optical beam passing through a pair of projection lenses [L1 and L2], in a configuration similar to a Badal system, that project the adjustable lens [AL] on the pupil of the patient's eye [E]. The first lens [L1] is positioned at a focal distance from the adjustable lens [AL] and the second lens [L2], which is identical to the first one, is placed at two focal distances from the first lens [L1]. The pupil of the eye [E] is positioned at a focal distance from the second lens [L2]. The referred distances are measured along the optical axis. With this configuration, it is achieved that the near vision channel preserves exactly its magnification, although it adopts different vergences as the adjustable lens changes its focus. In the image plane, all the images projected by the near vision channel have the same size, although their defocus-related blur level changes with the vergence induced by the adjustable lens.

To compensate for the fact that the projection system reverses the image in two axes, a reversing group of mirrors [RGM] is placed between the first lens [L1] and the second lens [L2] that reverses the image both vertically and horizontally while making the system more compact, preserving the distance between the projection lenses [L1 and L2] (along the optical axis). The reversing group of mirrors [RGM] used in this embodiment of the invention is conceptually similar to a pair of Porro prisms used in terrestrial observation prismatic telescopes, although implemented with mirrors instead of prisms to reduce weight and chromatic effects.

Figure 7:
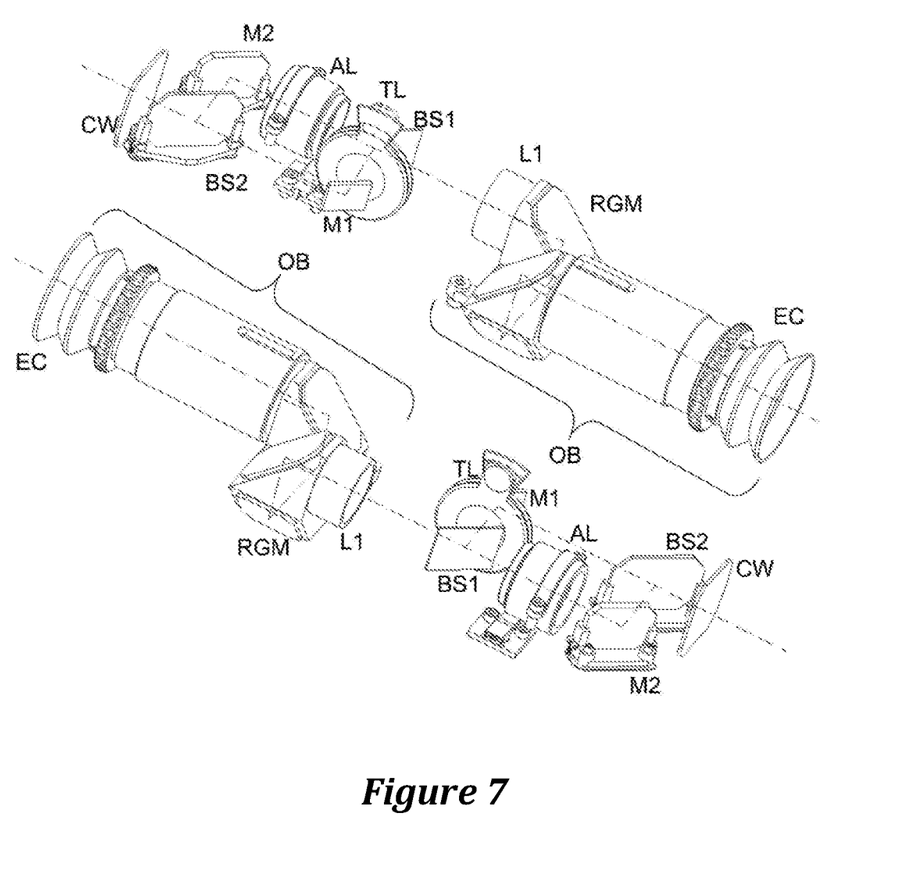

In an evolution of the same example, FIG. 7 shows the main elements of said miniature instrument, based on the embodiment shown in FIG. 2. The figure describes a single monocular system, but two complementary views from different angles are shown. The projection system, with the first lens [L1], the reversing group of mirrors [RGM] and the second lens [L2] (not shown in the drawing, but placed after the reversing group of mirrors [RGM]) is grouped in an ocular block [OB], which also contains an eyecup [EC]. The ocular block provides a very robust and stable assembly, especially against misalignment, of the four mirrors and two lenses in it. The eyecup [EC] provides an intuitive use of the system, helping the patient to place the eye in the plane in which the adjustable lens is projected, at a focal distance from the second projection lens [L2], which is the last optical component of the system. The ocular block [OB] is designed so that the distance between the first projection lens [L1] and the second projection lens [L2] can be changed, preserving the distance between the second lens [L2] of the projection system and the eyecup [EC] and preserving the alignment between all the elements. Thus, it is achieved that the projection lenses [L1 and L2] act as a Badal system affecting the two channels, the near vision channel and the far vision channel, which can be used to compensate for the refractive error of the patient.

As an alternative to the RGM of this example based on the use of mirrors, there are many other solutions for reversing the image in two axes, most of them using prisms, which could be used in other embodiments of the invention.

In the embodiment shown in FIG. 7, the size of the mirrors and beam splitters of the entire system are adapted to the size of the beam passing through them, considering the range of powers of the adjustable lens, ranging from −2 to +5 diopters, and the field of view, of 20 degrees.

FIG. 7 also shows the position within the far vision channel of the trial lenses [TL], which constitute an additional mechanism for refractive errors compensation, including astigmatism, and for which the system has also a specific support. The optomechanical components holding and positioning the optical elements [BS2 and M2] that are more important for the alignment between channels are also shown. These parts have been designed in order to enable and ensure the alignment in a robust, accurate and simple way. The system contains a closing glass window [CW], to protect the beam splitter closest to the object and maintain the cleanliness of its surface and the position that guarantees the alignment between channels. The connector that supplies power to the adjustable lens [AL] is also shown, which is a standard electrical connector located on a simple integrated circuit.

Figure 8:
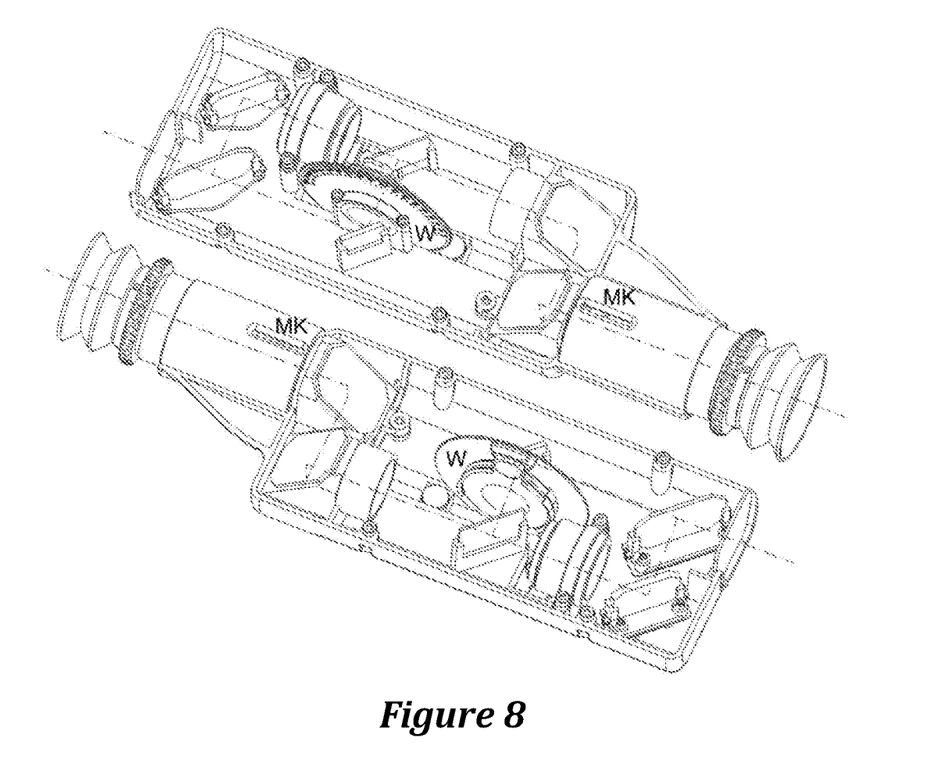

FIG. 8 shows the same embodiment of the invention with more detail, again in two complementary views of a single monocular system. The bottom housing on which all elements constituting the system are supported is shown. For all these elements, which have been detailed above, all the support or coupling pieces to the housing are shown. The support system for the trial lenses occupies the central part of the instrument, consisting of a rotating wheel [W] with which the angle of the astigmatism-correcting lens can be regulated. The rotating wheel [W] has a mark indicating the angular position where the trial lens has to be placed, and an angular scale that indicates the angle of the astigmatism induced to the patient.

The ocular block has also a mark [MK] and a scale, visible in FIG. 8, indicating the diopters of spherical refractive error that are compensated for the patient, up to 10 diopters of myopia or hyperopia, by changing the distance between the projection lenses [L1 and L2]. Although not visible in the figure, the system has an insert in its bottom side that provides a standard thread for attaching tripods.

This particular embodiment of the invention utilizes manufacturing tolerances of 0.05 mm, with which sufficient accuracy in the alignment of the elements is achieved, and has a matt black finished interior cavity to reduce the impact of the reflexes that inevitably occur in the optical elements. The system measures 280×83×75 min, weighs less than 400 grams, and has a reduced cost.

Example 2

FIG. 3 shows a simplified embodiment of the invention, in which the optical channels are kept separate from the instrument to the object, and which does not have a reversing group of elements. The main advantage of this simplified embodiment with respect to what is shown in FIG. 2 is the decrease in weight, volume and cost. As disadvantages, the object image is reversed, and may be subject to parallax when observing near objects, as the optical axes of the near and far vision channels do not match in the object space.

Example 3

FIG. 5 shows an embodiment of the invention in which the modality of temporal channel multiplexing, on the physical basis of a single optical channel, is exclusively used. The adjustable lens, when beating periodically two levels of optical power corresponding to far vision distance and near vision distance, generates two temporal channels that project component images with different degrees of focus that, since temporally overlapped at a frequency higher than the fusion frequency of the human visual system, generate the perception of a single image of simultaneous vision.

As the adjustable lens [AL] is directly projected by the projection lenses [L1 and L2] on the pupil of the subject's eye [E], it is guaranteed that all the image-forming channels (which are temporal in this case) have the same magnification independently of the focus of the adjustable lens and the beam vergence and therefore all the component images have the same size. The image reversion can be achieved by a reversing group of elements, not shown in FIG. 5.

Example 4

Figure 6:
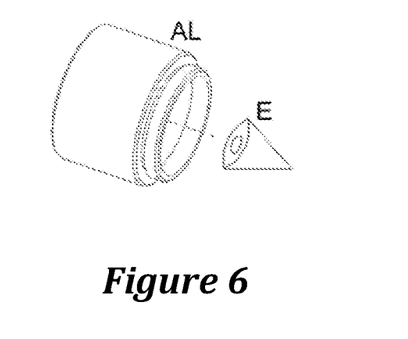
FIG. 6.—Device of the invention that represents the maximum simplicity of the solution based on the modality of temporal channel multiplexing with adjustable lens. The adjustable lens [AL] is located immediately in front of the eye [E] as an ophthalmic lens, trial lens or phoropter, without using projection systems.

FIG. 6 shows another embodiment of the invention, which represents the maximum simplicity of the solution based on the modality of temporal channel multiplexing with adjustable lens. In this embodiment the adjustable lens [AL] is located immediately in front of the eye [E] as an ophthalmic lens, trial lens or phoropter, without using projection systems. This configuration allows simulating bifocal, multifocal of progressive simultaneous vision corrections, reducing volume, weight and cost. However, the absence of projection lenses implies that different powers cause different magnifications in the different temporal channels and therefore different sizes of the corresponding component images. Furthermore, there is less versatility for correcting the refractive error of the patient.

The invention claimed is:

1. A miniature simultaneous vision simulator instrument comprising at least two image-forming channels, each one of which projects onto the retina of the same eye a component image of the same observed object with a different degree of defocus, so that the superposition of all the component images forms on the retina of the eye a final simultaneous vision image, characterized in that:
   at least one adjustable variable focus lens that, by changing its focus, modifies the vergence of the light beam passing through said adjustable lens, and
   at least one of the image-forming channels goes through the adjustable variable focus lens.

2. The instrument according to claim 1 wherein at least two of the image-forming channels are provided to the eye through two physically differentiated optical channels, and in at least one of them an adjustable lens is located.

3. The instrument according to claim 1 wherein:
   at least one of the adjustable variable focus lenses induces a periodic temporal variation in the vergence of the light beam passing through it,
   the different periodic vergence values define different temporal channels, each temporal channel being an image-forming channel that projects on the retina of the eye a component image of the observed object with a different degree of defocus corresponding to the beam vergence,
   the temporal channels are temporally multiplexed at a frequency higher than the fusion frequency of the eye, and
   the spacio-temporal overlap of all the component images forms a final simultaneous vision image that is perceived as static.

4. The instrument according to claim 1 comprising at least two physically differentiated optical channels and at least two temporal channels, wherein all the component images projected on the retina by the different image-forming channels from different temporal channels and different physically differentiated optical channels are spacio-temporally overlapped on the retina to form a final simultaneous vision image that is perceived as static.

5. The instrument according to claim 1 adapted for simulating a certain through-focus power pattern, selected between bifocal, multifocal and progressive.

6. The instrument according to claim 1 wherein the adjustable variable focus lens is placed immediately in front of the eye as an ophthalmic lens without using projection optics and wherein the adjustable variable focus lens induces different temporal channels multiplexed at a frequency higher than the fusion frequency of the eye.

7. The instrument according to claim 1 wherein the adjustable variable focus lens is optically projected onto the plane of the pupil of the eye via a projection optical system.

8. The instrument according to claim 1 wherein the instrument is a binocular instrument characterized by comprising two instruments entirely fixed, each one of which corresponds to one of the eyes of a patient.

9. The instrument according to claim 1 comprising optical components selected among active optical elements, passive optical elements, trial lenses, artificial pupils, phoropters, eyepieces, transmission masks, phase plates, transmission filters, polarizing filters, deformable mirrors, spatial light modulators, light sources, displays, sensors, and others.

10. The instrument according to claim 1, wherein the instrument is used in combination with glasses, contact lenses, intraocular lenses, refractive surgery or other ophthalmic or surgical corrections.

11. The instrument according to claim 1, wherein the instrument is used as phoropter.

12. The instrument according to claim 1, wherein the instrument is used in combination with visual or psychophysical tests.

13. The instrument according to claim 1, wherein the instrument is used for evaluating the tolerance of patients to simultaneous vision corrections or for training the patient prior to simultaneous vision corrections implantation.

14. The instrument according to claim 1, wherein the instrument is used for determining or selecting the parameters of a simultaneous vision correction at its design time or during the selection of the most suitable correction for a particular patient or group of patients.

* * * * *